United States Patent
Cespedes et al.

(10) Patent No.: US 6,213,950 B1
(45) Date of Patent: Apr. 10, 2001

(54) MEASUREMENT OF VOLUMETRIC FLUID FLOW AND ITS VELOCITY PROFILE

(75) Inventors: Eduardo Ignacio Cespedes, Folsom, CA (US); Charles Theodoor Lanceé, Waarder; Antonius Franciscus Wilhelmus Van Der Steen, Rotterdam, both of (NL); Wenguang Li, Sugar Land, TX (US); Nicolaas Bom, Berkenwoude (NL)

(73) Assignee: EndoSonics Corporation, Rancho Cordova, CA (US)

( * ) Notice: Subject to any disclaimer, the term of this patent is extended or adjusted under 35 U.S.C. 154(b) by 0 days.

(21) Appl. No.: 09/297,538
(22) PCT Filed: Sep. 2, 1997
(86) PCT No.: PCT/NL97/00504
  § 371 Date: Jul. 2, 1999
  § 102(e) Date: Jul. 2, 1999
(87) PCT Pub. No.: WO98/19603
  PCT Pub. Date: May 14, 1998

(30) Foreign Application Priority Data

Nov. 1, 1996 (EP) .................................................. 96203050

(51) Int. Cl.[7] .................................................. A61B 8/00
(52) U.S. Cl. ............................................................ 600/454
(58) Field of Search ................................... 600/437, 443, 600/444, 447, 454, 455, 456

(56) References Cited

U.S. PATENT DOCUMENTS

| 5,363,850 | 11/1994 | Soni et al. . |
| 5,373,848 | 12/1994 | Melton, Jr. et al. . |
| 5,785,657 | * 7/1998 | Breyer et al. .......................... 600/454 |
| 5,876,342 | * 3/1999 | Chen et al. ........................... 600/443 |
| 6,012,458 | * 1/2000 | Mo et al. ............................. 600/437 |

FOREIGN PATENT DOCUMENTS 0 538 885  4/1993 (EP) .

OTHER PUBLICATIONS

Li et al., *1995 IEEE Ultrasonics Symposium Proceedings*, 2, 1515–1518 (Nov. 10, 1995).

* cited by examiner

*Primary Examiner*—Marvin M. Lateef
*Assistant Examiner*—Maulin Patel
(74) *Attorney, Agent, or Firm*—Leydig, Voit & Mayer, Ltd.

(57) ABSTRACT

A method to measure spatial fluid flow components and their velocity profiles in a number of locations in a cross-sectional area of a lumen or other body cavity by using ultrasound in which the cross-sectional area is interrogated by a plurality of ultrasonic beams; the estimation of the spatial flow components is obtained from a combination of estimations of axial, lateral and total flow; the estimation of one or more flow components is obtained through any combination of time-shift and decorrelation analysis of two or more beam-signals of the interrogating ultrasound transducer, and the estimation accuracy is further improved by the use of a reference decorrelation curve.

25 Claims, 9 Drawing Sheets

Fig 3  Illustration of the characteristic decorrelation for a single range.

$\rho_B$ = beam decorrelation (calibration curve) characterizing the transducer
$\rho_E$ = measured decorrelation in blood
$\alpha$ = decorrelation rate; $[\alpha]$ = mm$^{-1}$
$\beta$ = decorrelation slope; $[\beta]$ = s$^{-1}$
$v$ = blood velocity; $[v]$ = mm/s

MEASUREMENT OF VOLUMETRIC FLUID FLOW AND ITS VELOCITY PROFILE

The assessment of fluid flow in the human body is important for medical diagnosis. For example, blood velocity and the volumetric flow (i.e., the volume of blood flowing through a blood vessel, e.g., in liter per second) routinely assist clinical decisions.

Various ultrasound techniques can be used to measure the motion of scattering materials such as blood, body fluids and tissue. Ultrasound contrast agents can also be used to enhance signals from fluids with insufficient scatter properties. For example, blood velocity can be measured in a small volume using the Doppler principle. In echographic B-scanning, multiple estimates of blood velocity in the plane of the scan can be combined with the gray-scale echo image by colouring.

Miniaturised ultrasound transducers can be placed inside the lumen of a vessel or other body cavities to obtain a cross-sectional echo image. The same ultrasound echo signals can be used to measure the velocity of the flowing blood or other fluids.

The purpose of the invention is to provide a method for measuring volumetric fluid flow and its velocity profile in a lumen or other body cavity. According to the invention an ultrasonic method is provided to measure volumetric flow through a lumen by accomplishing simultaneously and in situ (in place) the steps of a) measuring the local velocity of the scattering medium perpendicular to the ultrasound scan plane and b) integrating such velocity measurements over the area of the lumen.

An approximation to the above method in accordance with the invention comprises the steps of a) calculating the average value of the velocity of the scattering medium perpendicular to the ultrasound scan lane, b) calculation of the area of flow, and c) multiplying the average velocity by the area to obtain volume flow.

Furthermore, in order to reduce the number of calculations, the average velocity can be approximated by measurement of the velocity in a sub-region of the area of flow smaller than the total area of flow, and volume flow can be computed as before.

In the method according to the invention the scattering fluid of interest may be blood. For purposes of explaining the invention, the invention shall be discussed in relation to blood. Other fluids may be measured in a similar manner. Blood is composed by red blood cells (RBCs), white blood cells and platelets suspended in a liquid called plasma. Because the size and density of RBCs is large compared to that of white cells and platelets, backscatter of blood is attributed to the red blood cells. The measurement of blood velocity comprises the steps of:

a) obtain (transmit pulse and receive echo) two or more subsequent echo signals from a single (or a slightly changed) position of the ultrasound transducer at controlled interval(s) of time $\Delta t$, b) measure one or more displacements of the blood relative to the beam, $\Delta d$, and c) compute velocity from the ratios of displacements over the time interval, $v=\Delta d/\Delta t$.

One embodiment of the invention relates to the measurement of volumetric flow and velocity imaging from within the lumen of a blood vessels using intravascular ultrasound. It has to be mentioned here that conventional ultrasound has already been proposed to measure blood velocity on the plane of the scan. The scan is usually oriented along the blood vessel. If the scan plane is oriented perpendicular to the blood vessel, volumetric flow could also be computed as describe hereinafter.

The invention will be described in details with reference to the accompanying drawings, in which.

Figure 1:
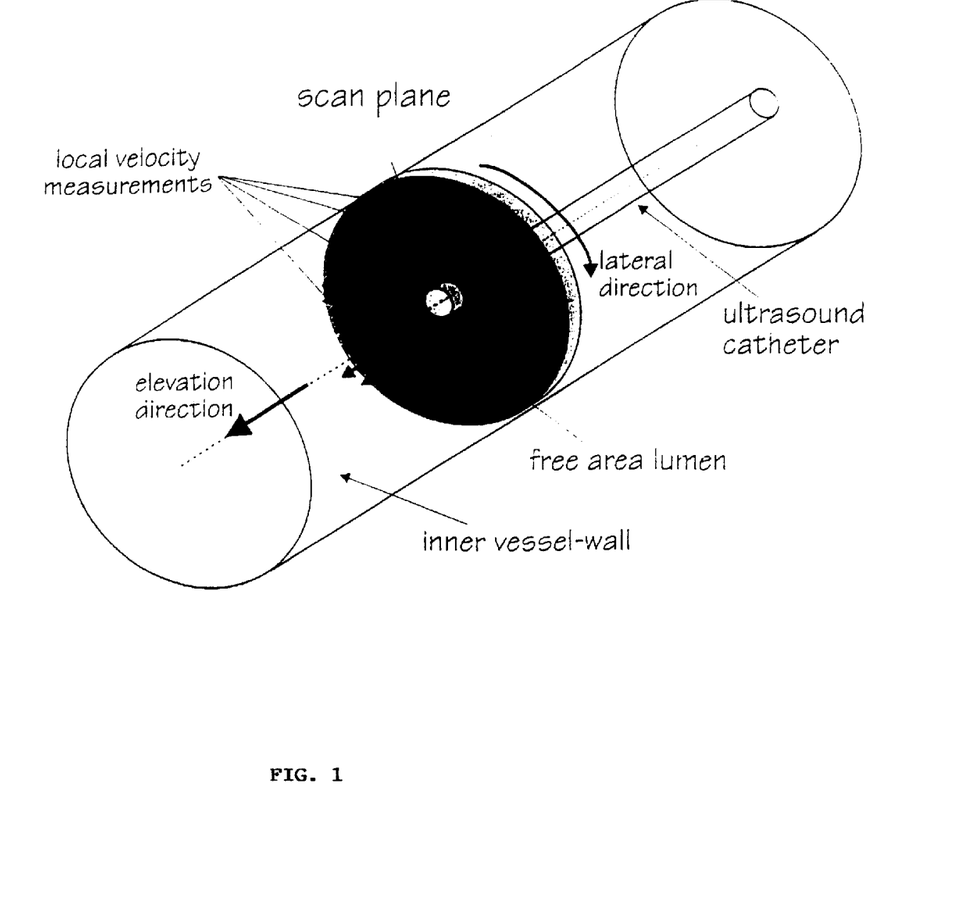
FIG. 1 is a schematic view of a lumen in which an ultrasound catheter is positioned.

Local estimates of blood velocity are obtained by means of echo-signal decorrelation and time-shift analysis. By means of an ultrasound transducer, a sound pulse is transmitted into the scattering medium; backscattered echoes from the medium are received by the same (or a separate transducer) and converted to an electric signal suitable for storage and processing. In FIG. 1 a rotational scan of the beam of a transducer is depicted.

The velocity of a moving object can be calculated by measuring the displacement of the object during a given interval of time. The ratio of displacement and time interval is the velocity.

The displacement of an ultrasound-scattering material (such as blood) moving through the beam of an ultrasound transducer results in concomitant changes in the received echo signal. For example, FIG. 2a shows a sequence of five echo signals (S1 through S5) obtained in an experiment where a scattering material is progressively displaced through an ultrasound beam. It can be observed that with increasing displacement, the echo signals progressively a) shift (advance) in time; and b) change in shape (FIG. 1a).

The correlation coefficient $\rho$ is a measure of the similarity (or dissimilarity) between a pair of signals and is defined such that $\rho=1$ (100%) when there is total similarity, and $\rho=0$ when the signals are note related at all. A decrease in correlation is termed decorrelation.

In an experimental example, the four correlation coefficients (or simply correlation for short) computed between echo-signal pairs S1–S2, S1–S3, S1–S4, and S1–S5 are shown in FIG. 2b. Correspondingly, the progressive time shift between the same echo signal pairs is computed and shown in FIG. 2c, In this experiment the time interval was $\Delta t=250$ $\mu s$. In general the time interval must be sufficiently short to warrant recognition of the advance in time and shape change of the echo signals: that is, if the time intervals is long relative to the velocity, the echo signal will change drastically precluding measurement of time shift and decorrelation.

Echo decorrelation is mainly a function of the beam characteristics (the width of the beam among others). For example, for a beam with beam width of 1 mm, the echo signal would be totally decorrelated after a 1 mm displacement of the scattering medium; however, a different transducer with a beam width of 2 mm would maintain some of the correlation after a 1 mm displacement since the scatterers are still within the beam width.

Figure 3:
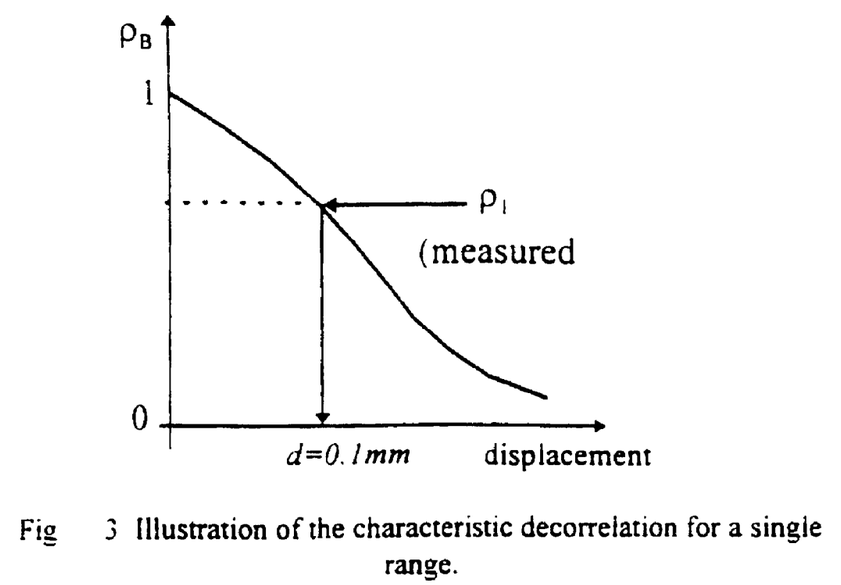
FIG. 3 is an illustration of the characteristic decorrelation for a single range.

Beam characteristics are range dependent. Consequently, an ultrasound beam exhibits a range-dependent decorrelation characteristic. By experimentally or theoretically assessing the decorrelation for a transducer at all ranges and for displacements in all directions we obtain what we can call the "characteristic decorrelation" of the beam. Once the characteristic decorrelation has been assessed, measured decorrelations in blood or tissue can be converted to displacement. For example, for a given range and direction of displacement across a particular beam, a characteristic decorrelation curve is illustrated in FIG. 3; in this example, a measured decorrelation value of $\rho_1$ would correspond to a displacement of d=0.1 mm.

Thus, the decorrelation characteristic of the transducer serves the purpose of a calibration factor which can be used to convert measured decorrelations into displacement and velocity.

One or more echo decorrelation values can be involved in the computation of a velocity value. Using a single decorrelation value between a single pair of echo signals, the velocity is computed as the ratio of the displacement obtained from the characteristic decorrelation at a given time interval. Using the example in FIG. 3, of the time interval between the echo acquisitions giving rise to the decorrelation of value $\rho_1$ was $\Delta T=1$ ms, then the velocity v would be $d/\Delta T=0.01$ mm/0.001s=10 cm/s. In practice the decorrelation characteristic versus displacement function may not be easily described analytically i.e., by a formula or the formula may not be suitable for inversion (obtain displacement from decorrelation). However, pre-calculated values of characteristic decorrelation for small increments in displacement can be arranged in a "look-up" table: then, by "looking up" the decorrelation value in the table, the corresponding displacement can be obtained. This is termed the look-up-table (LUT) method. The LUT method makes no assumption regarding the shape of the characteristic decorrelation.

Estimation of velocity based on a single decorrelation value is very sensitive to errors caused by other sources of decorrelation that are not related to motion. However, by using the rate of change from two or more echo decorrelation values, improved accuracy and precision of estimates of velocity may be possible. Although the improvement in precision can be expected since there is an implicit averaging procedure taking place, the improved accuracy is specific to this application. This particular scheme for averaging multiple decorrelation estimates is mentioned as an example and is not intended to exclude the possibility to use other averaging procedures with similar improvement.

Curve-fitting algorithms can be applied where a curve is fitted over a number of decorrelation measurement: the simplest curve being a straight line.

Figure 4:
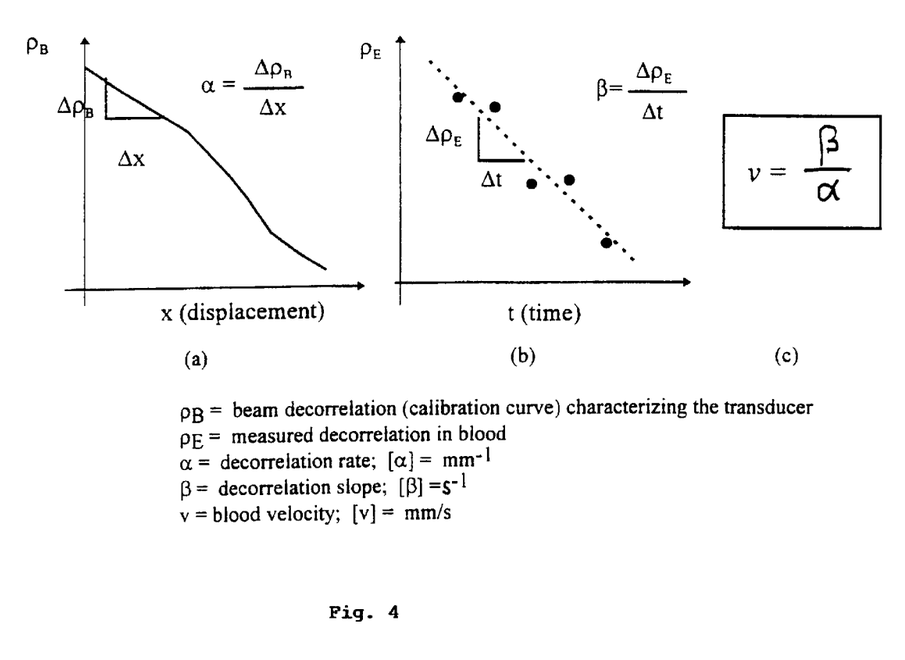
FIG. 4 is an illustration of the decorrelation "calibrated" velocity estimation procedure.

The linear fit method is illustrated in FIG. 4, where
a) a straight line is fitted over two or more decorrelation values. Since, by definition the decorrelation must be 1 for zero displacement, a single parameter (i.e., the slope of the line, termed the decorrelation slope), defines the curve formed by decorrelation measurements;
b) similarly, another straight line fit is performed in the corresponding area of the characteristic decorrelation curve; this yields a characteristic decorrelation rate; and
c) the ratio of the decorrelation slope and the characteristic decorrelation rate yields the velocity of blood (in units of mm/s).

FIG. 4 shows:
(a) Beam decorrelation estimated by experiment or theory; here shown only for one distance from the transducer.

(b) Decorrelation measured with ultrasound at five intervals of time (dots) with straight line fit.
(c) Velocity estimate using the decorrelation rate for the transducer from (a) and the decorrelation slope from the measurement (b) at corresponding depths.

When the curve formed by subsequent decorrelation measurement is not well approximated by a straight line, the linear-fit approach can lead to biased estimation. However, it follows from the above description that when a linear lit is inappropriate, a higher-order fit can be applied and more than one parameter is required to describe the best fit.

The LUT method with multiple decorrelation estimates involves the steps of
a) obtain from the characteristic decorrelation LUT the displacement for each measured decorrelation value obtained at subsequent time intervals; and
b) a straight line fit is performed on the displacement versus time interval plot. The slope of the straight line fit is the velocity of blood.

An alternative approach to that of fitting of a particular trend to the decorrelation measurements is to simply calculate the average of all available decorrelation estimates. It is important to recollect that the basic unit of the correlation algorithm is the cross-product of two echo signals. For a pair of discrete echo signals $s_1(i)$ and $s_2(i)$, the correlation coefficient is given by $$\rho = \frac{\sum_i s_1 \times s_2}{\sqrt{\sum_i s_1^2 \sum_i s_2^2}}.$$

Multiple decorrelation estimates can be made simultaneously by squaring the sum of a number of echo signals, since such operation yields a sum of cross-products. In order to illustrate this, we establish the relationship between the correlation coefficient and the normalized sum of squares as follows:

$$S = \frac{\sum_i (s_1 + s_2)^2}{\sum_i s_1^2 + \sum_i s_2^2}, \text{ and}$$

$$S = \frac{\sum_i s_1^2 + \sum_i s_2^2 + 2\sum_i s_1 s_2}{\sum_i s_1^2 + \sum_i s_2^2} = 1 + \frac{2\sum_i s_1 s_2}{\sum_i s_1^2 + \sum_i s_2^2}.$$

When the two terms in the denominator of the above equation are similar, their arithmetric and geometric mean values can also be assumed to be similar, thus $$1 \Big/ 2\Big[\sum_i s_1^2 + \sum_i s_2^2\Big] \approx \sqrt{\sum_i s_1^2 \sum_i s_2^2}.$$

Then we can write $$S \approx 1+\rho.$$

With the above formula, decorrelation can be estimated from the normalized sum of squares. When the squared sum involves more than two terms, additional factors weight in a the cross-products arise and depend on the number of terms in the square sum. For example, for the square sum of three echo signals obtained at intervals of time $\Delta t$, we get $$\sum_i (s_1 + s_2 + s_3)^2 = \sum_i [s_1^2 + s_2^2 + s_3^2 + 2s_1s_2 + 2s_2s_3 + 2s_1s_3] \approx$$

$$\sum_i [s_1^2 + s_2^2 + s_3^2 + 4s_1s_2 + 2s_1s_3]$$

since we can assume that $$\sum_i s_1 s_2 \approx \sum_i s_2 s_3.$$

Thus the correlation for echo signals spaced by a single time interval has a weighting factor of four, while for a spacing of two time intervals the weighting factor is two. This differential weighting of correlation at different time intervals must be taken into account to obtain an accurate estimate of the average decorrelation.

Similarly, decorrelation estimates can be obtained from the squared difference between echo signal pairs:

$$D = \frac{\sum_i (s_1 - s_2)^2}{\sum_i s_1^2 + \sum_i s_2^2},$$

and following similar steps as above, we obtain $$D \approx 1 - \rho$$

With the above formula, decorrelation can be estimated from the normalized squared difference of echo signals. In order to further simplify the calculation requirements, it is possible to substitute the absolute difference for the squared difference. In this way, the operation of calculating square values is avoided.

Note that while prior art teaches that decorrelation can be used to assess displacement, the improvement in accuracy due to the combination of multiple decorrelation values is novel.

For the purpose of measuring volumetric flow, the velocity component of the flow normal (perpendicular) to the scan plane must be assessed. Alternatively, the angle between the scan plane and the flow must be assessed.

Figure 5:
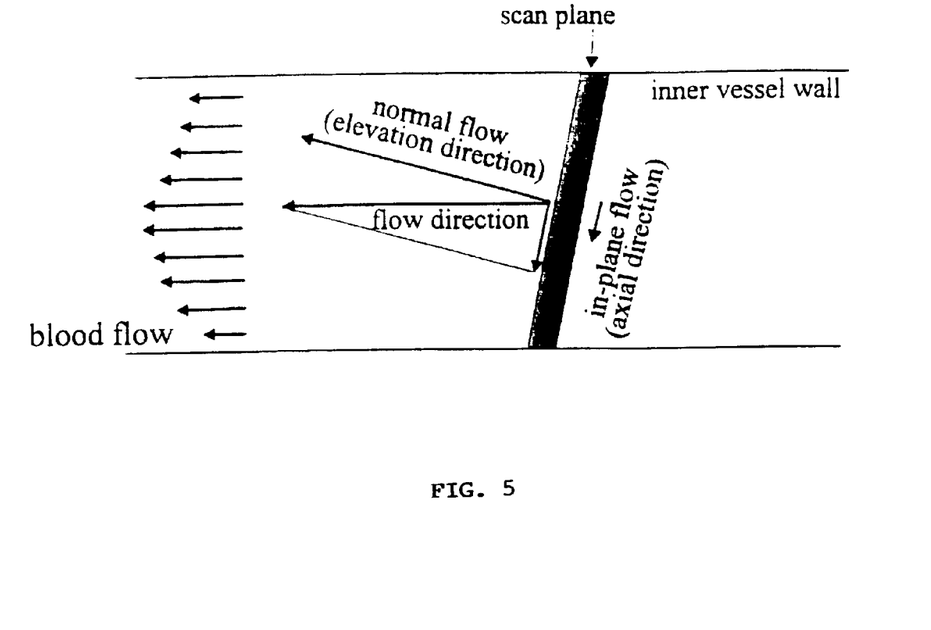
FIG. 5 is a schematic view of a lumen and the scan plane in such lumen.

This is illustrated for the vascular application in FIG. 5. The blood velocity must be computed for blood velocity imaging, but the normal flow component must be computed for volumetric flow estimation.

Figure 6:
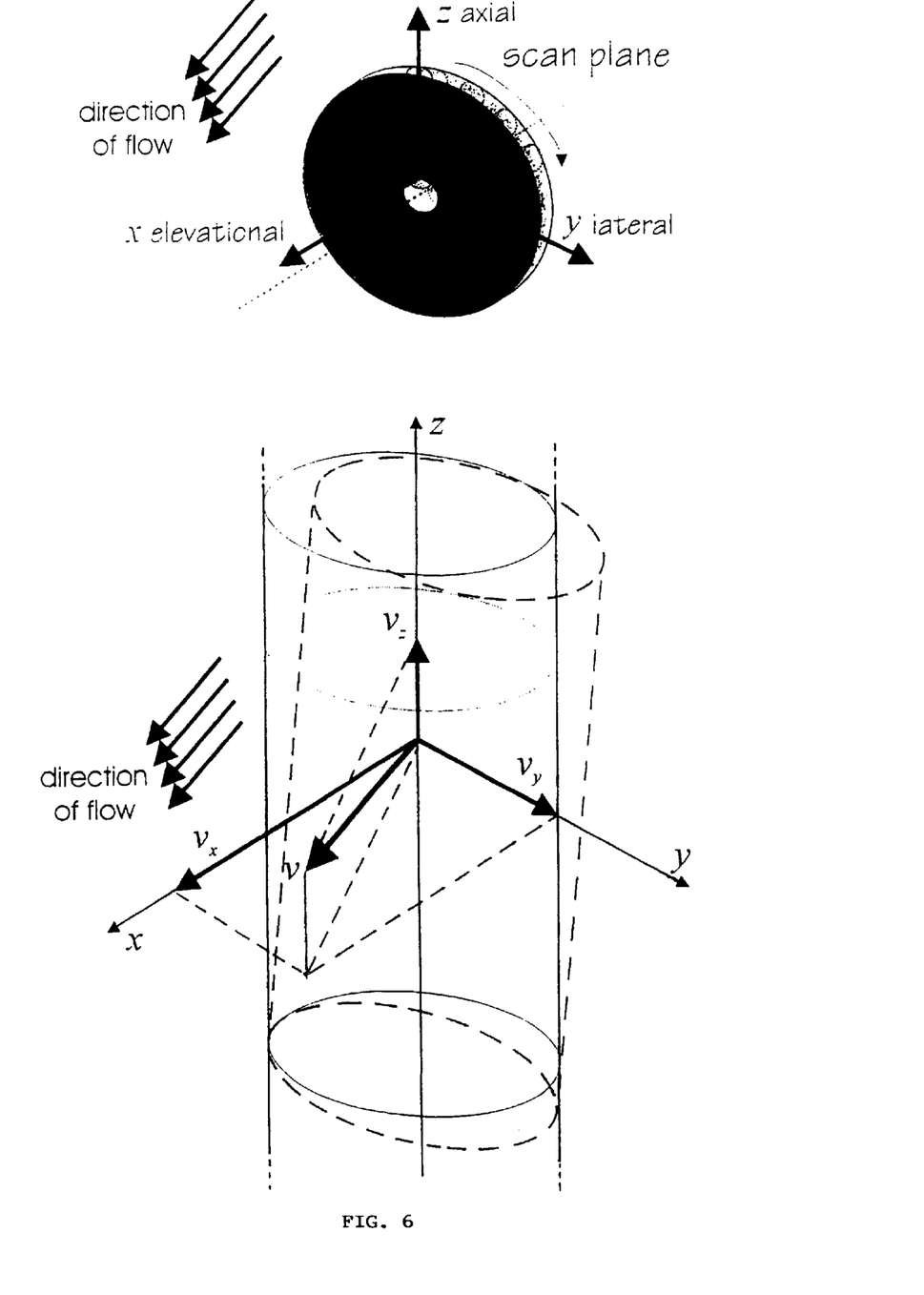
FIG. 6 illustrates the direction of flow relative to the three-dimensional orthogonal axes centered on the transducer aperture.

In general, the direction of flow can have any arbitrary angle with respect to the reference axes of the ultrasound beam. This is illustrated in FIG. 6 where the direction of flow is shown relative to the three-dimensional orthogonal axes centered on the transducer aperture. These axes in combination with the direction of the scan (sweeping of the beam) give rise to three spatial directions that are termed axial, lateral, and elevational (FIG. 6). When a scattering medium displaces exclusively along the axis of the transducer (axial displacement), the motion can be assessed from the time shift of the echo signal when axial decorrelation is sufficiently low. When the motion occurs exclusively across the axial direction of the transducer, the echo signal decorrelates as the original scattering blood particles move out of the beam and new blood particles move into the beam. Displacement across the beam and in the scan plane is termed lateral displacement. Displacement across the beam and across the scan plane is termed elevational displacement.

Axial, lateral and elevational displacements introduce echo decorrelation giving rise to axial, lateral and elevational decorrelation components. Additionally, axial displacement introduces a time shift. Thus, in order to fully characterize displacement with respect to a scan plane, all these decorrelation components must be computed. Axial and elevational displacement can be measured as described above. Lateral displacement can be estimated by "cross-decorrelation", that is decorrelation analysis between echo signals from adjacent beam locations within the scan plane. The relationship between these decorrelations must also be assessed experimentally or theoretically.

In a hypothetical example, assuming a linear decorrelation with displacement, lateral and elevational decorrelations can be combined in the squared sense (that is, the square of the total decorrelation is the sum of the square of the lateral and elevational decorrelations); then, knowing the lateral displacement from cross-decorrelation analysis the elevational component of displacement can be isolated.

Analogously, the presence of axial, lateral and elevational velocity components can be considered. It is important to note that for the purpose of measuring volumetric flow, the velocity component normal to the scan plane must be assessed. When the direction of flow is not perpendicular to the scan plane (elevation direction), flow velocity estimated with decorrelation may lead to biased estimation of volume flow (unless the angle between the direction of flow and the scan plane is assessed).

In the common practice of intravascular ultrasound, the main component of displacement is in the elevational direction. Thus, the contribution of axial and lateral displacements may be neglected in some circumstances without significant deterioration of the velocity estimates However, the contribution of lateral and axial components should be kept under consideration. These components can increase during the examination of curved vessels and when secondary flow is present, among other possibilities.

Echo signal decorrelations also occurs due to sources that are unrelated to motion. For example, electronic noise present in the echo signals results in decorrelation. Two echo signals can differ only due to corruption of independent realisations of the noise source. Thus, for improved estimation of velocity from decorrelation, decorrelation from sources of non-motion-related decorrelation must be isolated.

By computing the decorrelation of echoes from stationary tissue (e.g., vessel wall), the decorrelation due to sources other that motion can be assessed. Then, this decorrelation can be deducted from the total decorrelation measured from moving blood (under the assumption that blood and tissue echo signals contain the same amounts of electronic and quantization noise).

The main goal of the invention is to determine volumetric flow and velocity of blood with respect to the vessel through which it flows. However, the above scheme estimates velocity with respect to the beam under the assumption that the transducer is fixed in position within the vessel. Normally, the transducer can and will move with the pulsation of flowing blood, adding an undesired motion component. In order to improve velocity estimation, the motion of the transducer with respect to the vessel wall must also be assessed. Transducer motion can be assessed by measuring the time shift of echoes from quasi-static (relative to the high velocity blood) vessel wall tissue.

In general, the local velocity of blood varies within the vessel lumen; that is, blood tends to move slower near static features (e.g., the vessel wall, the ultrasound catheter) and faster away from those features (e.g., towards the center of the free lumen). Thus, to fully characterize flow it is important to estimate blood velocity in a localized manner (note: commonly used Doppler-based techniques for flow estimation are based on the estimation of the peak value of the velocity within the lumen and the assumption of a velocity distribution).

Figure 2:
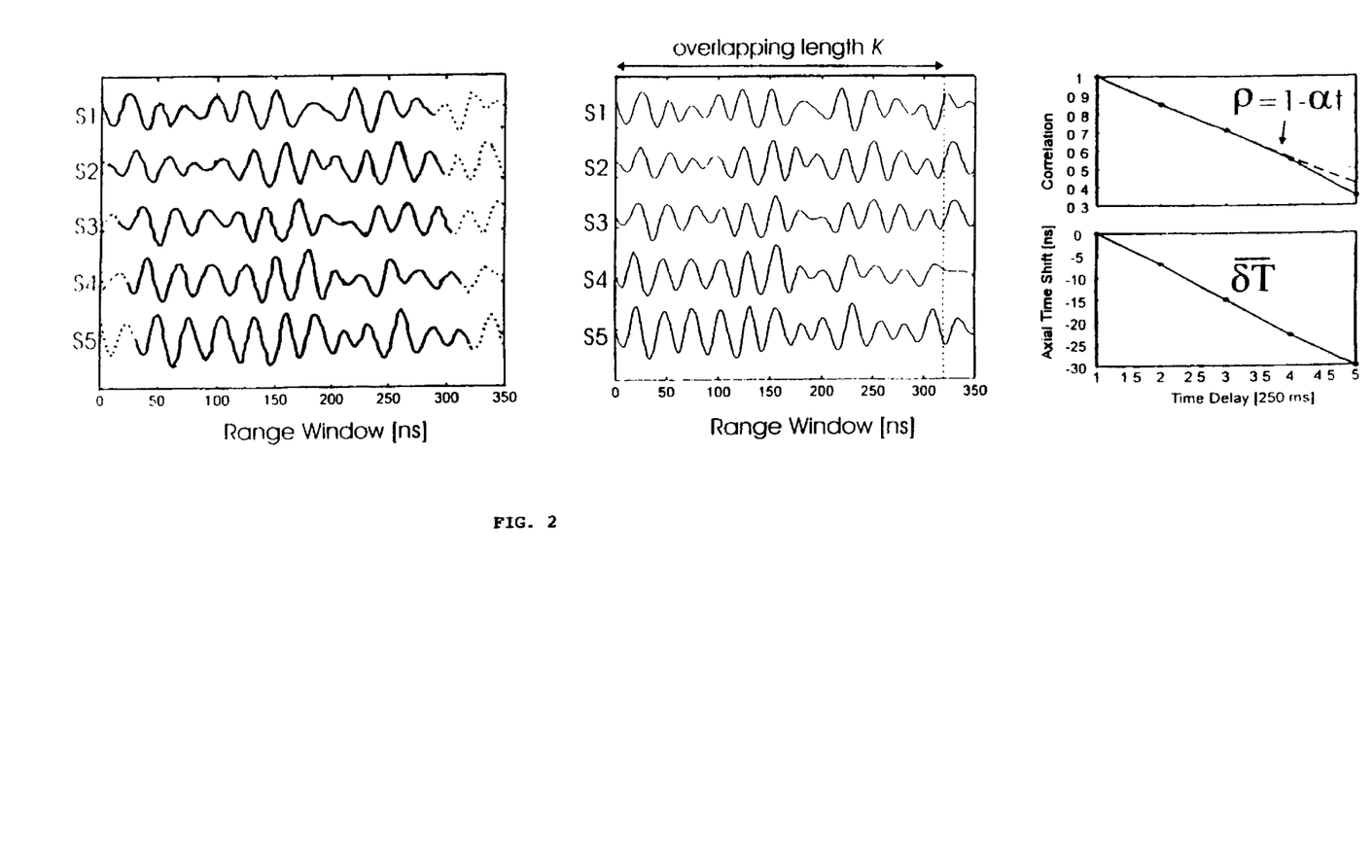
FIGS. 2a–2c are graphs of echo-signals received by an ultrasound transducer and of the time shift between echo-pairs.
Figure 7:
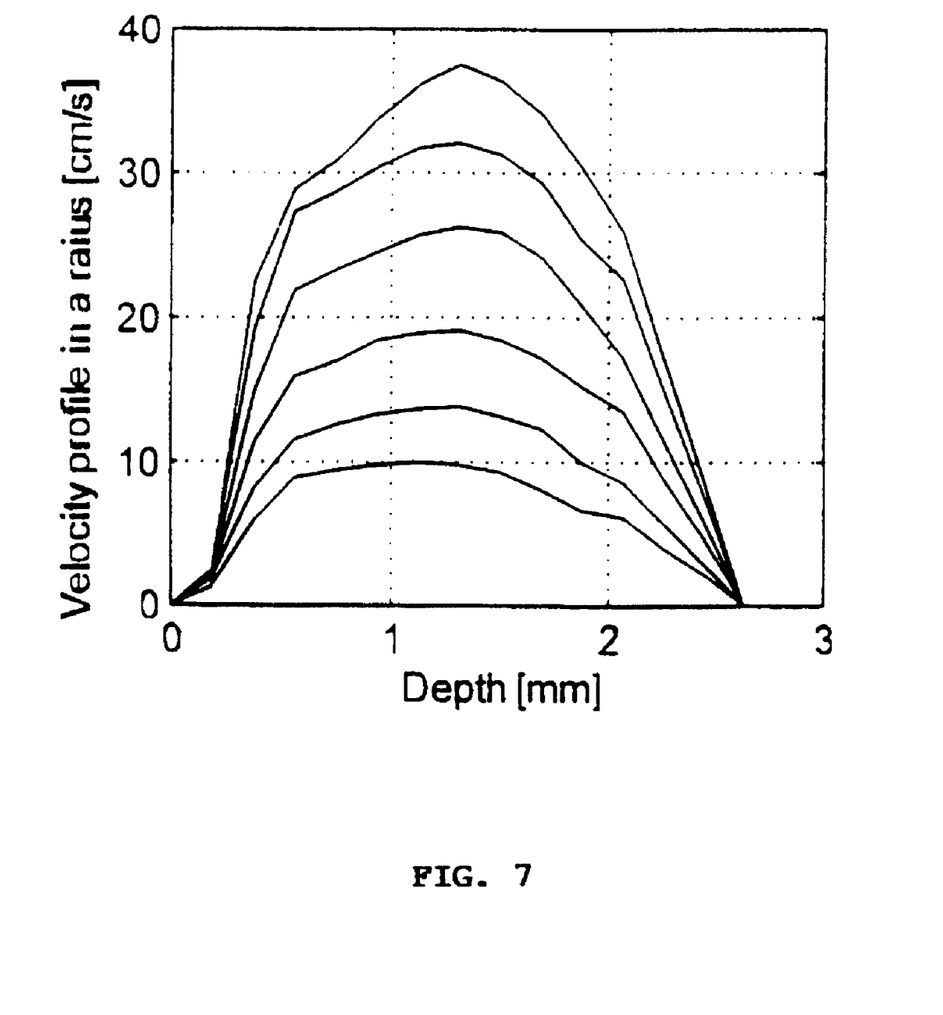
FIG. 7 is a graph showing velocity profiles at different flow velocities.

Blood motion measurement scan be achieved in a localized manner by analysis of gated (i.e., for "small" segments of) echo signals which corresponds to the local motion of small parts of the blood volume For example, FIG. 2 shows gated signals representing echoes from 0.25 mm of blood. Many such local estimates of blood are measured in adjacent regions along the beam and can be combined to form a "velocity profile". Velocity profiles obtained at different flow velocities are shown in FIG. 7: note the higher velocities near the center and low velocities towards the static wall. Adjacent beam positions in a scan plane can be used to form a map or image velocity. The sweeping of the beam (scanning) can be achieved a) by physically moving the transducer,
b) by physically moving a mirror which reflects the beam of a static transducer, or
c) by electronically generating of the beam using an array of transducers elements.

Figure 8:
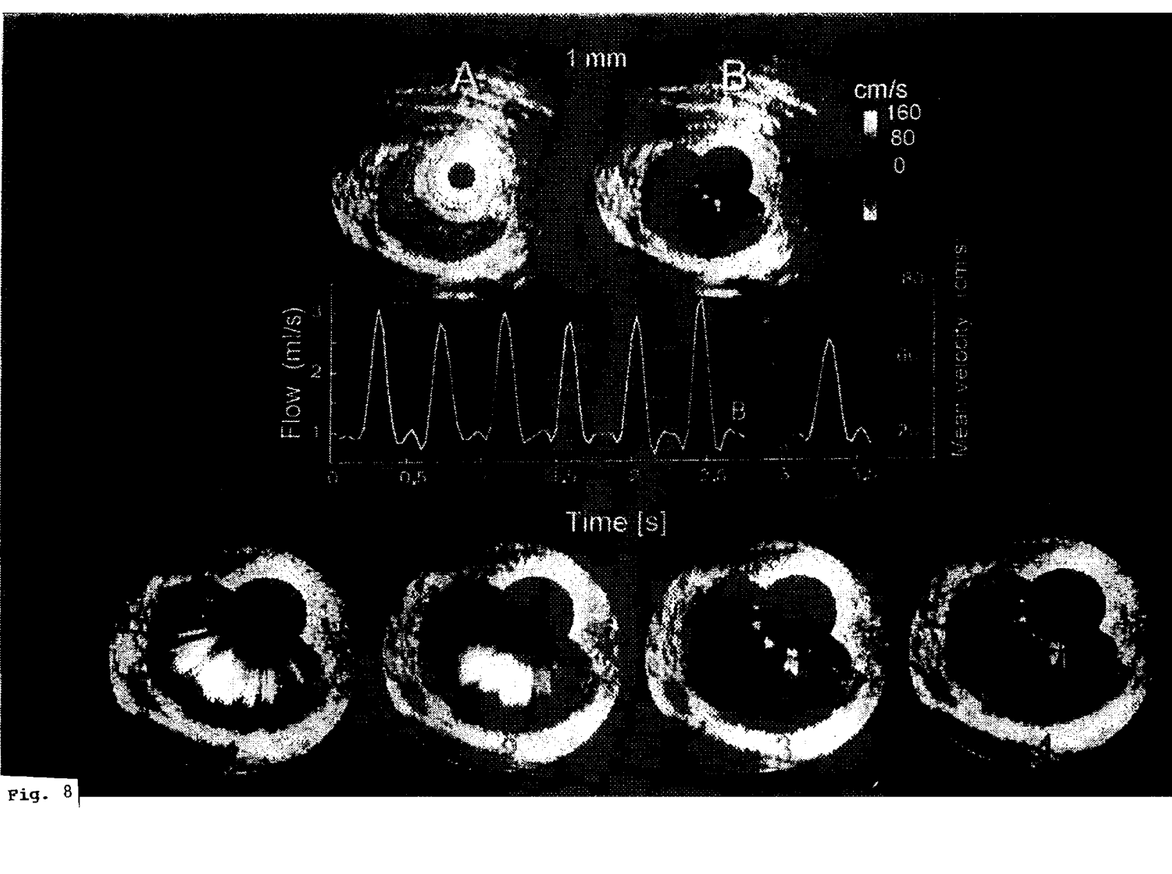
FIG. 8 shows different flow velocity images computed within one heart cycle.

Velocity images can be superimposed on the gray-scale image of static tissues by coloring image pixels according to the magnitude of flow. For example, from an experiment conducted in a live pig, four flow velocity images computed within one heart cycle are shown in FIG. 8a. Thus, unlike any previously described method, an image of the velocity of blood flowing normal to the cross-section of the scan plane is obtained (illustration in FIG. 1, measurement in FIG. 8).

Additionally, velocity components or the volume flow can be converted into an audible signal in order to provide a different way to present flow information. For example, a converter could be used to transform flow data into an analog signal which, following amplification, could drive a loudspeaker. This may be a useful feature when the operator is unable to look at the monitor while manipulating the ultrasound transducer. For instance, the range and mean value flow velocity could be represented by the bandwidth and the pitch of the output sound. This presentation of flow information is analogous to what is used in Doppler systems where the frequency of the Doppler signal is by default in the audible range and needs only be amplified and connected to a speaker. However, here the sound is synthesized from independently computed flow information.

Additionally, decorrelation based estimation of motion can be used to differentiate areas where there is moving blood (that is, the free lumen area) from areas where tissue is static. Blood flows at a much higher velocity relative to the motion of healthy or diseased tissue (such as the vessel wall, plaques and dissections).

The prior art in the intravascular ultrasound application describes the combined use of two catheters to measure volumetric flow. A first intravascular ultrasound catheter is used to measure free lumen area and is not capable of measuring flow. A second Doppler-ultrasound catheter is used to assess the velocity of blood flow and is not capable of measuring the area of flow. Additionally, the Doppler catheter cannot measure local velocity at many spatial locations: a velocity profile within the lumen is not measured but assumed based on a single measurement of velocity (peak or mean).

The combination of measured area and assumed velocity distribution yields volumetric flow. However, the cross-sectional area measurement and the flow estimation are performed at two spatially separated locations. Alternatively, cross-sectional area can be measured in one location of the vessel, and later the velocity can be measured in that same location. Thus, the prior art is limited to either "simultaneous" or "in place" measurements, but does not teach both.

In the current invention integration of the measured velocity map over all points in a cross-section of the free lumen area yields the volume of blood flowing through the vessel. Since the area of integration and the flow velocity is computed from the same signals, it is a fact that the estimation of area and velocity are simultaneous and in place.

Alternatively, a reduced, but representative number of points within a cross-section of the free lumen area can be used to estimate the average value of flow velocity in the entire free lumen area. The average velocity can be estimated from a partial area of the flow area when the velocity distribution is known to first approximation. Simultaneously, the area of flow can be calculated at the same cross-section. The area of flow times the average flow yields the volume of blood flowing through the vessel. Like in the Doppler approach, a velocity profile within the lumen must be assumed to calculate the average velocity based on a restricted number of measurements of velocity within the lumen. However, unlike the Doppler approach, in this alternative implementation velocity and flow are measured simultaneously and in place.

Since this measurement can be performed at regular intervals that are small compared to the period of the heart or respiratory cycle, phasic volumetric flow can be assessed (phasic meaning the time history within a cycle). Phasic volumetric flow measured in a live-pig experiment is shown in FIG. 8b.

The relationship between local blood pressure and the volumetric flow yields additional hemodynamic information on extreme clinical relevance. Particularly, the change of the pressure-flow relationship in response to vaso-active drugs is used to investigate the reaction of different parts of the vasculature. For this reason, several methods have been developed that combine pressure-sensing catheters with intravascular Doppler-ultrasound assessment of volumetric flow. Alternatively, lumen area or diameter can be used as an estimator of pressure and velocity can be used as a measure of volumetric flow. A limitation common to current multi-variable methods is the inability to assess the hemodynamic variables coincidentally in time and space. Additionally, multiple catheter approaches suffer from possible interference between devices: for example, in the combination of intravascular ultrasound for area measurement and Doppler catheter for velocity measurement, the intravascular catheter disturbs the blood flow and therefore affects the velocity that is measured by the Doppler catheter.

Figure 9:
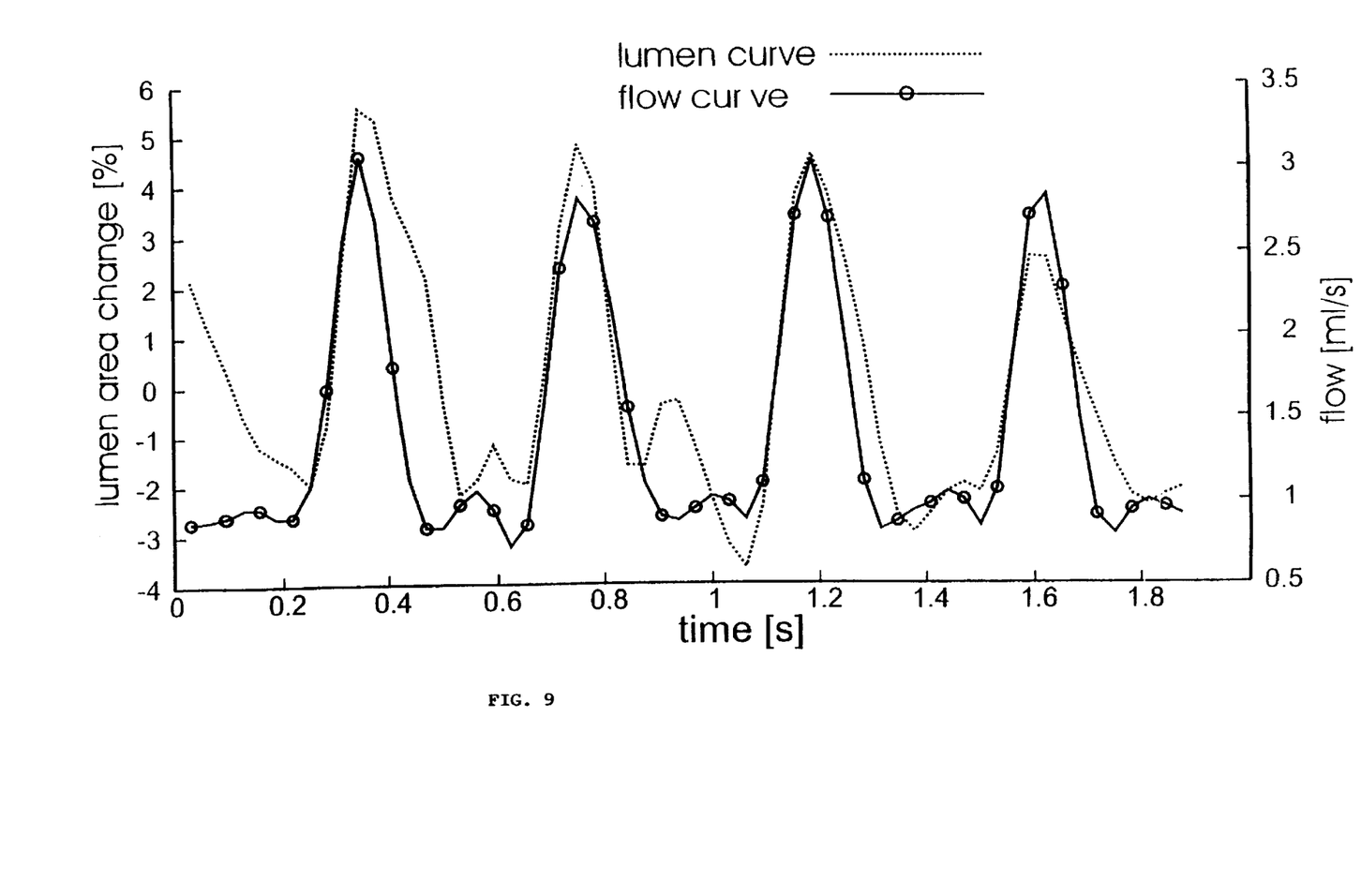
FIG. 9 is a graph showing simultaneous calculation of phasic cross-sectional area and phasic volumetric flow.

Since the endoluminal pressure is intimately related to the change in cross-sectional lumen area (particularly, there is a linear relationship between pressure and lumen diameter toward late diastole), this invention can provide concurrent and coplanar measurements of cross-sectional lumen area and volumetric flow. This is shown in FIG. 9 where phasic cross-sectional area and phasic volumetric flow were calculated simultaneously and from the same scan plane from the live pig experiment. The phasic relationship between area and flow can provide information on the resistance of the vasculature. Spectral analysis of phasic area and flow can be used to assess arterial impedance.

So far the measurement of flow has been described assuming that the backscatter from blood is uniform within the lumen and in time. However, normally red blood cells tend to form clusters, a process called aggregation, and arrange themselves in "strings" called rouleaux. In the following blood, rouleaux are positioned along the direction of flow. The presence of RBC aggregation and rouleaux is a function of the cyclic variation of the local shear: regions of high shear (near static structures) have low aggregation and areas of low shear (near the center of the free lumen) have high aggregation. Thus, a spatial distribution of RBC aggregation as well as a cyclic temporal variation with the heart rate are known to exist. In intravascular ultrasound imaging, these effects are manifested as a cyclic and spatial variation of the echo intensity (since larger aggregates of RBCs also backscatter stronger echoes). Thus, examination of the echo intensity and the backscatter coefficient function can yield information about the scatterer aggregation.

The shape and size of the back scattering particles can also have a significant effect on the decorrelation phenomenon. Clearly, the echo from a single point scatterer moving across a beam will decorrelate faster than the echo arising from a long string of aligned scatterers moving across the same beam. Thus, the dependence of decorrelatlon on blood backscatter should be compensated for improved accuracy in volume flow and velocity estimation. For example, long rouleaux or clusters present in the central (low shear) part of the free lumen would result in local underestimation of velocity.

Analoaously to the determination of the characteristic decorrelation of an ultrasound beam, for each shape and size of scatterers we can obtain a "scatterer characteristic decorrelation" function. Then, from the scatterer type/shape can be estimated from backscatter analysis and the velocity estimates can be compensated for scatterer characteristic decorrelation.

The effect of RBC aggregation on decorrelation is a function of the size of the aggregate relative to the wavelength. Therefore, applications that utilize high frequency ultrasound (i.e., wavelengths similar to the aggregate size) may be expected to experience a higher dependence on aggregation. Conversely, low ultrasonic frequencies (i.e., wavelengths much larger than the RBC diameter) may be expected to be less affected by aggregation-dependent decorrelation. In practice, reasonable estimates of flow can be obtained without backscatter-dependent compensation.

What is claimed is:

1. A method to measure spatial fluid flow components and their velocity profiles in a number of locations in a cross-sectional area of a lumen or other body cavity by using ultrasound characterized in that:
   a) interrogating the cross-sectional area by a plurality of ultrasonic beams;
   b) first estimating the spatial flow components obtained from a combination of estimations of axial, lateral and total flow;
   c) second estimating one or more flow components obtained through time-shift and decorrelation analysis of two or more beam-signals of the plurality of the ultrasonic beams of an interrogating ultrasound transducer; and
   d) accuracy of (b) or (c) is further improved by the use of a reference decorrelation curve obtained from experiments or beam-theory or both.

2. The method of claim 1, further characterized by simultaneous and in place estimation by the same means of the dimensions (cross-sectional area, mean diameter, etc.) of the flow area.

3. The method of claim 2, further characterized by combining the component of flow velocity normal to a cross-section of an area of flow in a number of spatial locations and the flow area as defined in claim 2 to derive a momentary value of volume flow.

4. The method of claim 2, further characterized by combining (1) the average over a number of spatial locations of the component of flow velocity normal to a cross-section of an area of flow and (2) the flow area as defined in claim 2 to derive a momentary value of volume flow.

5. The method of claim 2, further characterized by combining the component of flow velocity normal to a cross-section in a number of discrete spatial locations and the corresponding areas of said discrete spatial locations to derive a momentary value of volume flow.

6. The method of claim 5, wherein the step of combining normal velocity and corresponding discrete areas is an integration operation.

7. The method of claim 4, further characterized by calculation of the average component of flow velocity normal to a cross-section of a total area of flow from a partial section of said total area of flow.

8. The method of claim 7 wherein said partial section of said area of flow is a single line segment of said total flow area.

9. The method of claim 3, wherein a time history of volume flow and lumen dimensions are recorded within the heart cycle or the respiratory cycle.

10. The method of claim 1, characterized by the use of means to compensate for the decorrelation characteristic of a scattering medium.

11. The method of claim 1 characterized by the use of means to compensate for non-motion-related decorrelation components.

12. The method of claim 1 characterized by the use of means to compensate the velocity measurements for relative motion of a transducer with respect to relatively static tissues.

13. The method of claim 1 wherein the velocity is measured from the slope of the decorrelation.

14. The method of claim 1 wherein the velocity is measured from the slope of decorrelation-derived displacements.

15. The method of claim 1 wherein the decorrelation is derived from squared differences of echo signal calculations.

16. The method of claim 1 wherein the average decorrelation is derived from squared sums of echo signals.

17. The method of claim 1 wherein a velocity measurement is converted into an audible sound.

18. The method of claim 1 wherein the interrogating transducer is an intraluminal ultrasound transducer where the beam is scanned in a plane by one of the following
   a) rotating a transducer;
   b) rotating a mirror which redirects the beam of a static transducer;
   c) electronically generating the beam through a multi-element transducer without transducer motion; and
   d) a combination of a) and c).

19. The method of claim 1 wherein the plurality of ultrasound beams are scanned through adjacent spatial locations in a sequential step-wise way.

20. The method of claim 1 wherein the plurality of ultrasound beams are scanned through adjacent spatial locations in a non-sequential way.

21. The method of claim 1 wherein the plurality of ultrasound beams are scanned through adjacent spatial locations in a back and forth way.

22. The method of claim 1 wherein the transducer is a single element, a linear, annular or phased array.

23. The method of claim 1 wherein a velocity profile measurement is converted into an audible sound.

24. The method of claim 3 wherein volume flow is converted into an audible sound.

25. An apparatus for measuring spatial fluid flow components and their velocity profiles in a number of locations in a cross-sectional area of a lumen or other body cavity, comprising a catheter arranged for being located in such lumen or body cavity, said catheter having ultrasound transducer means at or near its distal end, said ultrasound transducer means comprising one of the following a) a rotatable transducer and means for rotating said transducer b) a static transducer and a rotatable mirror and means for rotating said mirror in order to redirect an ultrasound beam originating from said static transducer c) a multi-element transducer and means for successively electronicallly generating an ultrasound beam from different elements of said multi-element transducer, in order to create a plurality of ultrasonic beams for interrogating a cross-sectional area of a lumen or other body cavity in which the catheter may be located in practice, said apparatus further comprising means arranged for processing information obtained from said plurality of ultrasonic beams, said processing comprising the steps of 1) deriving estimation of axial, lateral and total flow from said ultrasonic beams and obtaining therefrom an estimation of spatial fluid flow components, through 2) time-shift and decorrelation analysis of two or more beam-signals of the ultrasound transducer, and 3) improving an estimation accuracy through use of a reference decorrelation curve obtained from experiments or from beam-theory or both.

* * * * *